(12) United States Patent
Kwon et al.

(10) Patent No.: US 10,046,619 B2
(45) Date of Patent: Aug. 14, 2018

(54) DUST SENSOR FOR VEHICLE

(71) Applicants: Hyundai Motor Company, Seoul (KR); ONEGENE ELECTRONICS, Hwaseong, Gyeonggi-do (KR)

(72) Inventors: Dong Ho Kwon, Gyeongsangbuk-do (KR); Gee Young Shin, Gyeonggi-do (KR); Kwang Woon Cho, Gyeonggi-do (KR); Dong Won Yeon, Gyeonggi-do (KR); Young Oh Kim, Gyeonggi-do (KR); Hyun Hoo Jang, Chungcheongnam-do (KR); Jin Young Lee, Gyeonggi-do (KR)

(73) Assignees: Hyundai Motor Company, Seoul (KR); ONEGENE ELECTRONICS, Hwaseong, Gyeonggi-do (KR)

( * ) Notice: Subject to any disclaimer, the term of this patent is extended or adjusted under 35 U.S.C. 154(b) by 19 days.

(21) Appl. No.: 15/272,643

(22) Filed: Sep. 22, 2016

(65) Prior Publication Data
US 2017/0297405 A1   Oct. 19, 2017

(30) Foreign Application Priority Data
Apr. 14, 2016   (KR) .................. 10-2016-0045299

(51) Int. Cl.
*B60H 1/00* (2006.01)
*G01N 21/13* (2006.01)
(Continued)

(52) U.S. Cl.
CPC ............. *B60H 1/008* (2013.01); *G01N 21/13* (2013.01); *G01N 21/53* (2013.01); *G01N 2021/152* (2013.01)

(58) Field of Classification Search
CPC ........ B60H 1/008; G01N 21/13; G01N 21/53; G01N 2021/152
See application file for complete search history.

(56) References Cited

U.S. PATENT DOCUMENTS

| 4,733,605 A * | 3/1988 | Holter | B01D 53/34 |
| | | | 454/158 |
| 2005/0282486 A1* | 12/2005 | Takeda | B60H 1/247 |
| | | | 454/158 |
| 2012/0117745 A1* | 5/2012 | Hattori | B60S 1/0848 |
| | | | 15/250.01 |

(Continued)

FOREIGN PATENT DOCUMENTS

| JP | 2008-267974 A | 11/2008 |
| JP | 2015-224032 A | 12/2015 |

(Continued)

*Primary Examiner* — Mussa A Shaawat
(74) *Attorney, Agent, or Firm* — Mintz Levin Cohn Ferris Glovsky and Popeo, P.C.; Peter F. Corless

(57) ABSTRACT

A dust sensor includes: a main body in which a dust inlet is formed and including an optical sensor and a lens for collecting light scattered by dust which enters into the main body through the dust inlet; a button unit protruding outwardly from the main body and having one end that is inserted into a coupling hole formed in the main body, wherein the button unit is selectively moved, by a pushing operation of a user, upward and downward with respect to an interior of the main body in which the lens is installed; and a cleaner installed on the one end of the button unit that is inserted into the main body, wherein the cleaner is repeatedly brought into contact with the lens by the upward and downward movement of the button unit.

9 Claims, 3 Drawing Sheets

(51) Int. Cl.
 *G01N 21/53* (2006.01)
 *G01N 21/15* (2006.01)

(56) References Cited

U.S. PATENT DOCUMENTS

| 2013/0219742 | A1* | 8/2013 | Field | B60S 1/0848 34/491 |
|---|---|---|---|---|
| 2014/0009616 | A1* | 1/2014 | Nakamura | H04N 7/18 348/148 |
| 2014/0036132 | A1* | 2/2014 | Pawlowski | H04N 5/2171 348/335 |
| 2015/0090291 | A1* | 4/2015 | Na | B60S 1/56 134/6 |
| 2015/0343999 | A1* | 12/2015 | Lopez Galera | B08B 3/02 134/30 |
| 2015/0344001 | A1* | 12/2015 | Lopez Galera | B60S 1/56 134/198 |
| 2016/0059674 | A1* | 3/2016 | Kim | B60K 35/00 701/36 |
| 2016/0282874 | A1* | 9/2016 | Kurata | G05D 1/0289 |
| 2017/0113517 | A1* | 4/2017 | Kwon | B01D 46/0041 |
| 2017/0276592 | A1* | 9/2017 | Kwon | G01N 15/1429 |
| 2017/0313286 | A1* | 11/2017 | Galera | B60S 1/56 |

FOREIGN PATENT DOCUMENTS

| KR | 10-0169231 B1 | 10/1998 |
| KR | 2004-0084739 A | 10/2004 |
| KR | 10-0729344 B1 | 6/2007 |
| KR | 10-0836725 B1 | 6/2008 |
| KR | 10-2010-0104784 A | 9/2010 |
| KR | 10-2014-0023068 A | 2/2014 |

* cited by examiner

DUST SENSOR FOR VEHICLE

CROSS-REFERENCE TO RELATED APPLICATION

This application claims under 35 U.S.C. § 119(a) the benefit of and priority to Korean Patent Application No. 10-2016-0045299 filed on Apr. 14, 2016, the entire contents of which are incorporated herein by reference as it fully set forth herein.

BACKGROUND

(a) Technical Field

The present disclosure relates generally to a dust sensor for vehicles and, more particularly, to a dust sensor for vehicles which is configured such that dust deposited on a lens can be effectively removed.

(b) Background Art

Generally, air conditioning systems are designed for purifying contaminated air and converting it to fresh air, and are configured to suck contaminated air using a fan and collect fine dust or bacteria using a filter, thereby removing body odor, the smell of smoke, and so forth. In such an air conditioning system, a dust sensor senses the concentration and size of dust contained in the air in the passenger compartment and determines whether the operation of the air conditioning system should be started depending on the degrees of the concentration and size of dust. Based on the determination, the rotational speed of the fan is controlled. Therefore, the air conditioning system can appropriately purify contaminated air in the passenger compartment, and the operation thereof can be efficiently implemented.

Meanwhile, the dust sensor can be provided with an optical unit including a light emitting unit which generates light, a light receiving unit which senses light scattered by dust, a lens which collects scattered light into the light receiving unit, and a blocking filter which blocks visible rays from light that has passed through the lens. In this regard, a heater controller equipped in a vehicle is configured such that dust which is sensed by the light scattering method enabled by the above-mentioned configuration is removed according to predetermined control logic, including control logic pertaining to the operation of the air conditioning, and, simultaneously, alarms depending on the concentration of dust can be provided to a driver so that the driver may effectively recognize the concentration of dust.

However, in such a dust sensor, if the surface of the lens is contaminated by dust drawn into the dust sensor, the dust makes it difficult to sense scattered light in the dust sensor, thus causing a reduction of the sensing performance. Therefore, a structure capable of easily cleaning the lens is required.

The above information disclosed in this Background section is only for enhancement of understanding of the background of the disclosure, and therefore it may contain information that does not form the related art that is already known in this country to a person of ordinary skill in the art.

SUMMARY OF THE DISCLOSURE

The present disclosure has been made in an effort to solve the above-described problems associated with the related art.

An object of the present disclosure is to provide a dust sensor for vehicles which employs a separate button structure provided with a spring, so that a cleaner installed on a button can be selectively brought into contact with the surface of a lens by a button pushing operation of a user, whereby dust deposited on the lens can be easily removed.

According to embodiments of the present disclosure, a dust sensor for a vehicle includes: a main body in which a dust inlet is formed and including an optical sensor and a lens for collecting light scattered by dust which enters into the main body through the dust inlet; a button unit protruding outwardly from the main body and having one end that is inserted into a coupling hole formed in the main body, wherein the button unit is selectively moved, by a pushing operation of a user, upward and downward with respect to an interior of the main body in which the lens is installed; and a cleaner installed on the one end of the button unit that is inserted into the main body, wherein the cleaner is repeatedly brought into contact with the lens by the upward and downward movement of the button unit.

The button unit may include: an up-down movable member fitted into a coupling protrusion protruding from an upper surface of the main body and configured to move upward and downward along a longitudinal direction of the coupling protrusion; and an insert member extending from the up-down movable member to have a predetermined length, bent at the end of the insert member and inserted into the coupling hole, the insert member having one end that is adjacent to the lens at which an installation region is provided for installation of the cleaner.

The button unit may further include an elastic member enclosing an outer circumferential surface of the coupling protrusion and configured to provide an elastic force to the up-down movable member to enable the insert member to move upward or downward in the coupling hole.

The insert member may be formed to have a width greater than a width of the coupling hole and may be provided with hook parts on opposite sides thereof to allow the insert member to be inserted into the coupling hole while the hook parts are compressed inwardly.

The hook parts may respectively include locking protrusions so that, when the up-down movable member moves upward or downward, the insert member which is inserted into the coupling hole is locked in the main body by the locking protrusions.

The insert member may be made of an elastic material such that the insert member is bendable while the cleaner cleans the lens.

The cleaner may be made of a cotton material, such as a piece of cloth, and may be replaceable.

Furthermore, in accordance with embodiments of the present disclosure, a vehicle includes: the dust sensor configured as described above, and a control unit including a memory to store program instructions and a processor to execute the stored program instructions and configured to control operation of a heating, air conditioning, and ventilation (HVAC) system equipped in the vehicle based on information sensed by the dust sensor.

Other aspects and preferred embodiments of the disclosure are discussed infra.

Advantageously, the present disclosure uses a separate button structure provided with a spring, so that a cleaner installed on a button can be selectively brought into contact with the surface of the lens by a button pushing operation of the user, whereby dust deposited on the lens can be easily removed. Furthermore, because scattered light can be effectively sensed in the dust sensor through the lens from which dust has been removed, the problem of degraded performance of the dust sensor can be fundamentally prevented.

BRIEF DESCRIPTION OF THE DRAWINGS

The above and other features of the present disclosure will now be described in detail with reference to embodiments thereof illustrated the accompanying drawings which are given hereinbelow by way of illustration only, and thus are not limitative of the present disclosure, and wherein.

Figure 1:
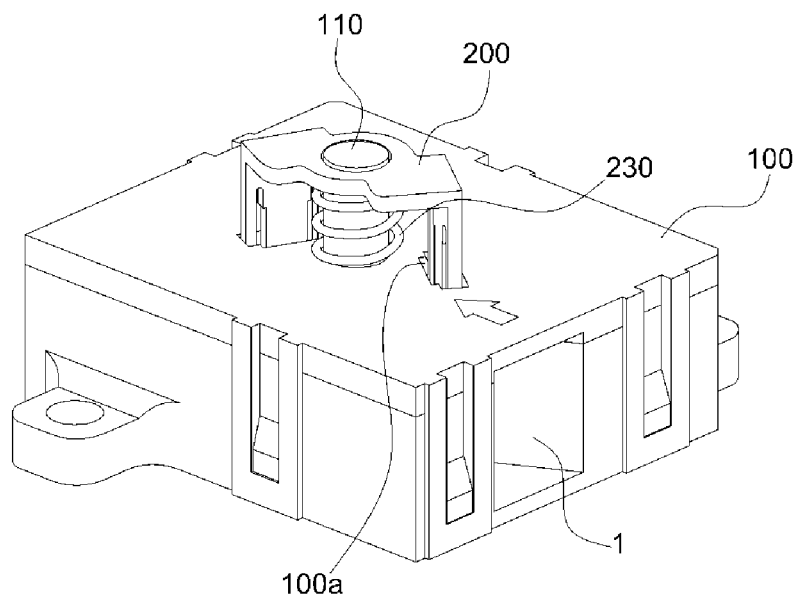
FIG. 1 is a view schematically illustrating a dust sensor for vehicles according to embodiments of the present disclosure.

It should be understood that the appended drawings are not necessarily to scale, presenting a somewhat simplified representation of various preferred features illustrative of the basic principles of the disclosure. The specific design features of the present disclosure as disclosed herein, including, for example, specific dimensions, orientations, locations, and shapes will be determined in part by the particular intended application and use environment.

In the figures, reference numbers refer to the same or equivalent parts of the present disclosure throughout the several figures of the drawing.

DETAILED DESCRIPTION OF THE EMBODIMENTS

Hereinafter reference will now be made in detail to various embodiments of the present disclosure, examples of which are illustrated in the accompanying drawings and described below. While the disclosure will be described in conjunction with exemplary embodiments, it will be understood that present description is not intended to limit the disclosure to those exemplary embodiments. On the contrary, the disclosure is intended to cover not only the exemplary embodiments, but also various alternatives, modifications, equivalents and other embodiments, which may be included within the spirit and scope of the disclosure as defined by the appended claims.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. Further, in the following detailed description, names of constituents, which are in the same relationship, are divided into "the first," "the second," etc., but the present disclosure is not necessarily limited to the order in the following description. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g., fuels derived from resources other than petroleum). As referred to herein, a hybrid vehicle is a vehicle that has two or more sources of power, for example both gasoline-powered and electric-powered vehicles.

Additionally, it is understood that one or more of the below methods, or aspects thereof, may be executed by at least one control unit (not shown). The term "control unit" may refer to a hardware device that includes a memory and a processor. The memory is configured to store program instructions, and the processor is specifically programmed to execute the program instructions to perform one or more processes which are described further below. Moreover, it is understood that the below methods may be executed by an apparatus comprising the control unit in conjunction with one or more other components, as would be appreciated by a person of ordinary skill in the art.

Furthermore, the control unit of the present disclosure may be embodied as non-transitory computer readable media containing executable program instructions executed by a processor, controller or the like. Examples of the computer readable mediums include, but are not limited to, ROM, RAM, compact disc (CD)-ROMs, magnetic tapes, floppy disks, flash drives, smart cards and optical data storage devices. The computer readable recording medium can also be distributed throughout a computer network so that the program instructions are stored and executed in a distributed fashion, e.g., by a telematics server or a Controller Area Network (CAN).

Figure 2:
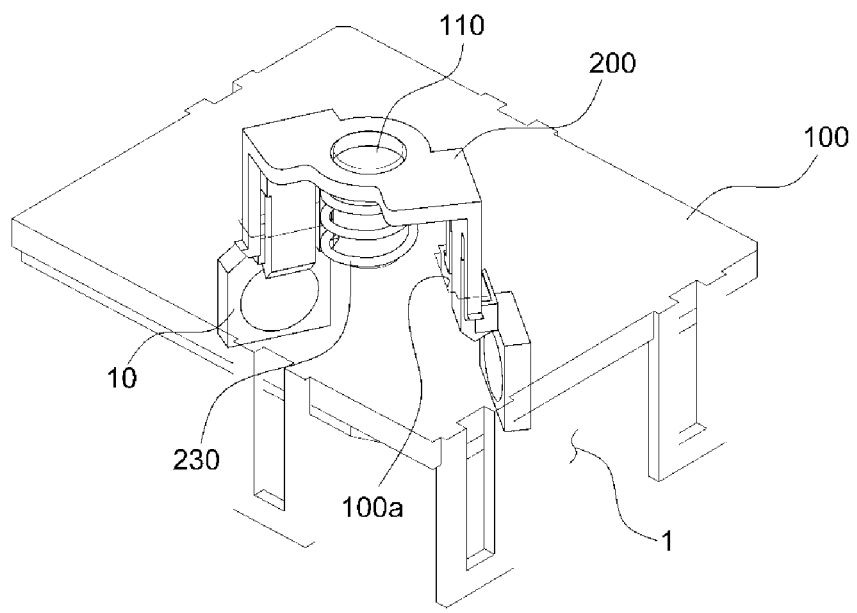
FIG. 2 is a view illustrating the interior of the dust sensor for vehicles according to embodiments of the present disclosure.
Figure 3:
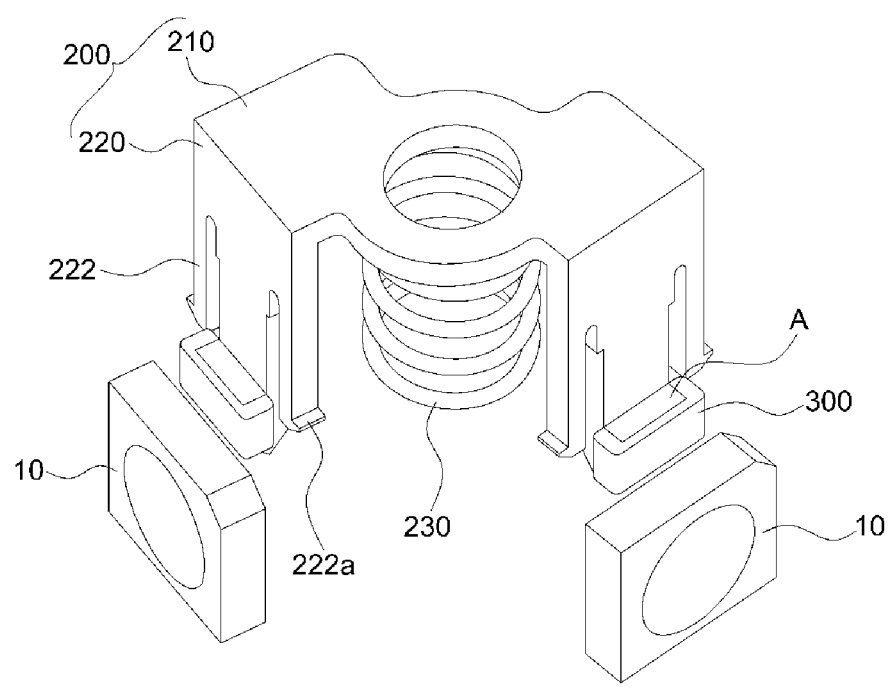
FIG. 3 is a view illustrating a button unit of the dust sensor for vehicles according to embodiments of the present disclosure.
Figure 4:
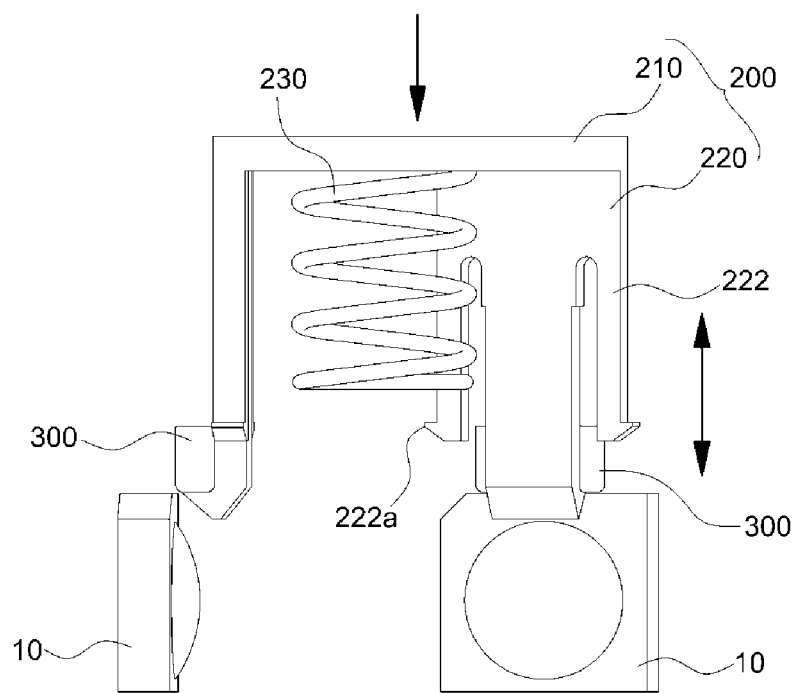
FIG. 4 is a view illustrating the operation of the button unit of the dust sensor for vehicles according to embodiments of the present disclosure.

Referring now to the presently disclosed embodiments, FIG. 1 is a view schematically illustrating a dust sensor for vehicles according to embodiments of the present disclosure. FIG. 2 is a view illustrating the interior of the dust sensor for vehicles according to embodiments of the present disclosure. FIG. 3 is a view illustrating a button unit of the dust sensor for vehicles according to embodiments of the present disclosure. FIG. 4 is a view illustrating the operation of the button unit of the dust sensor for vehicles according to embodiments of the present disclosure.

As shown in FIGS. 1 and 2, the dust sensor for vehicles includes a main body 100, a button unit 200 and a cleaner 300.

To measure characteristics, such as the concentration, etc., of dust which enters into the vehicle, the main body 100 has a dust inlet 1 formed at one side thereof, and includes an optical sensor and a lens 10 which collects light scattered by dust dawn into the main body 100 through the dust inlet 1.

The button unit 200 protrudes from an upper surface of the main body 100 in a state in which one end of the button unit 200 is inserted into a coupling hole 100*a* formed in the main body 100. The button unit 200 can be selectively moved, by a pushing operation of a user, upward and downward with respect to the interior of the main body 100 in which the lens 10 is installed.

In this regard, the coupling hole 100*a* into which the one end of the button unit 200 is inserted may be formed in the same direction as the direction in which the lens 10 is installed in the main body 100. Furthermore, the button unit 200 may be installed at a height at which, when it is moved downward, one surface of the button unit 200 inserted into the main body 100 can be disposed adjacent to the surface of the lens 10.

As shown in FIG. 3, the button unit 200 includes an up-down movable member 210, an insert member 220 and an elastic member 230.

The up-down movable member 210 is fitted into a coupling protrusion 110 which protrudes from the upper surface of the main body 100. The up-down movable member 210 is movable upward or downward along the longitudinal direction of the coupling protrusion 110.

To allow the insert member 220 to be easily inserted into a pair of coupling holes 100a formed in the upper surface of the main body 100, the up-down movable member 210 preferably has a predetermined shape taking into account the direction in which the insert member 220 is inserted.

The insert members 220, each of which has a predetermined length, are bent in a '¬' shape from respective opposite ends of the upper surface of the up-down movable member 210 and are inserted into the corresponding coupling holes 100a.

Furthermore, an installation region A is formed on each insert member 220 so that the cleaner 300 can be installed on the one end of the insert member 220 that is adjacent to the lens 10.

In detail, the cleaner 300 is installed on the one end of the insert member 220 such that the cleaner 300 is repeatedly brought into contact with the lens 10 by up and down movement of the up-down movable member 210. When the insert member 220 is moved downward in the main body 100 by the operation of pushing the up-down movable member 210, the cleaner 300 installed in the installation region A moves while wiping the surface of the lens 10, thus cleaning the surface of the lens 10.

In this regard, the cleaner 300 installed on the installation region A of the insert member 220 is preferably made of a cotton material such as a piece of cloth. If the cleaner 300 is contaminated by removal of dust from the surface of the lens 10, the cleaner 300 may be removed from the installation region A and replaced with another cleaner 300.

Such replacement of the cleaner 300 can be performed by displacing the insert member 220 from the coupling hole 100a. The insert member 220 is usually disposed to be locked in the coupling hole 100a of the main body 100 and thus is prevented from being undesirably removed from the coupling hole 100a. When the replacement of the cleaner 300 is required, removal of the insert member 220 from the coupling hole 100a can be allowed by manipulation of the user.

In detail, the insert member 220 has a width greater than the width of the coupling hole 100a, and hook parts 222 are provided on respective opposite sides of the insert member 220. When the insert member 220 is first installed, it is inserted into the coupling hole 100a in a state in which the hook parts 222 are compressed inward.

Locking protrusions 222a may be provided on the respective hook parts 222 so that, after the hook parts 222 have been compressed inward and the insert member 220 has been inserted into the coupling hole 100a, the insert member 220 can be prevented from being undesirably removed from the coupling hole 100a by elastic force when the insert member 220 moves upward and downward.

For this, each locking protrusion 222a is formed to protrude from one side of the corresponding hook part 222 and is configured such that when the insert member 220 is moved upward or downward by the elastic force of the elastic member 230, the insert member 220 can be locked to the coupling hole 100a.

The elastic member 230 is made of a spring and, as shown in FIG. 4, is installed to enclose the outer circumferential surface of the coupling protrusion 110. The elastic member 230 provides elastic force to the up-down movable member 210 so as to enable the insert member 220 to move upward or downward in the coupling hole 100a. That is, when the up-down movable member 210 is pushed downward, the insert member 220 moves downward in the coupling hole 100a, whereby the lens 10 can be cleaned by the cleaner 300 installed on the installation region A. When the up-down movable member 210 that has been pushed is released, the elastic member 230 returns to its original position by the elastic restoring force thereof. Therefore, the operation of pushing the up-down movable member 210 can be easily repeated.

In this regard, the insert member 220 is disposed such that the cleaner 300 comes into contact with the surface of the lens 10 so as to effectively clean the lens 10. Further, the insert member 220 is preferably formed of material having elastic force to allow the insert member 220 to be bent as the cleaner 300 cleans the lens 10 along the curved surface of the lens 10.

With regard to such an operation of cleaning the lens 10 installed in the dust sensor for vehicles, the cleaning operation may be periodically performed through the operation of pushing the button unit 200 by a service center staff when an engine oil change is performed. In addition, a vehicle owner may periodically push the button unit 200, thus cleaning the lens 10. In this way, because the lens 10 can be always maintained in a clean state through periodic maintenance, the problem of a reduction in performance of the dust sensor can be fundamentally prevented.

The present disclosure uses a separate button structure provided with a spring, so that the cleaner installed on the button unit can be selectively brought into contact with the surface of the lens (e.g., by a button pushing operation of the user), whereby dust deposited on the lens can be easily removed. Furthermore, in the present disclosure, because scattered light can be effectively sensed in the dust sensor through the lens from which dust has been removed, the problem of degraded performance of the dust sensor can be fundamentally prevented.

The disclosure has been described in detail with reference to embodiments thereof. However, it will be appreciated by those skilled in the art that changes may be made in these embodiments without departing from the principles and spirit of the disclosure, the scope of which is defined in the appended claims and their equivalents.

What is claimed is:

1. A dust sensor for a vehicle comprising:
   a main body in which a dust inlet is formed and including an optical sensor and a lens for collecting light scattered by dust which enters into the main body through the dust inlet;
   a button unit protruding outwardly from the main body and having one end that is inserted into a coupling hole formed in the main body, wherein the button unit is selectively moved, by a pushing operation of a user, upward and downward with respect to an interior of the main body in which the lens is installed; and
   a cleaner installed on the one end of the button unit that is inserted into the main body, wherein the cleaner is repeatedly brought into contact with the lens by the upward and downward movement of the button unit.

2. The dust sensor of claim 1, wherein the button unit includes:
an up-down movable member fitted into a coupling protrusion protruding from an upper surface of the main body and configured to move upward and downward along a longitudinal direction of the coupling protrusion; and
an insert member extending from the up-down movable member to have a predetermined length, bent at an end of the insert member, and inserted into the coupling hole, the insert member having one end that is adjacent to the lens at which an installation region is provided for installation of the cleaner.

3. The dust sensor of claim 2, wherein the button unit further includes:
an elastic member enclosing an outer circumferential surface of the coupling protrusion and configured to provide an elastic force to the up-down movable member to enable the insert member to move upward or downward in the coupling hole.

4. The dust sensor of claim 2, wherein the insert member is formed to have a width greater than a width of the coupling hole and is provided with hook parts on opposite sides thereof to allow the insert member to be inserted into the coupling hole while the hook parts are compressed inwardly.

5. The dust sensor of claim 4, wherein the hook parts respectively include locking protrusions so that, when the up-down movable member moves upward or downward, the insert member which is inserted into the coupling hole is locked in the main body by the locking protrusions.

6. The dust sensor of claim 2, wherein the insert member is made of an elastic material such that the insert member is bendable while the cleaner cleans the lens.

7. The dust sensor of claim 2, wherein the cleaner is made of a cotton material.

8. The dust sensor of claim 2, wherein the cleaner is replaceable.

9. A vehicle comprising:
a dust sensor; and
a control unit including a memory to store program instructions and a processor to execute the stored program instructions and configured to control operation of a heating, air conditioning, and ventilation (HVAC) system equipped in the vehicle based on information sensed by the dust sensor,
wherein the dust sensor includes:
a main body in which a dust inlet is formed and including an optical sensor and a lens for collecting light scattered by dust which enters into the main body through the dust inlet;
a button unit protruding outwardly from the main body and having one end that is inserted into a coupling hole formed in the main body, wherein the button unit is selectively moved, by a pushing operation of a user, upward and downward with respect to an interior of the main body in which the lens is installed; and
a cleaner installed on the one end of the button unit that is inserted into the main body, wherein the cleaner is repeatedly brought into contact with the lens by the upward and downward movement of the button unit.

* * * * *